(12) United States Patent
Lundquist et al.

(10) Patent No.: US 8,394,435 B2
(45) Date of Patent: Mar. 12, 2013

(54) PREPARATION OF DOUGH-BASED PRODUCT

(75) Inventors: Henrik Lundquist, Malmo (SE); Tina Spendler, Malov (DK); Tine Hoff, Holte (DK)

(73) Assignee: Novozymes A/S, Bagsvaerd (DK)

( * ) Notice: Subject to any disclaimer, the term of this patent is extended or adjusted under 35 U.S.C. 154(b) by 907 days.

(21) Appl. No.: 10/588,449

(22) PCT Filed: Jan. 20, 2005

(86) PCT No.: PCT/DK2005/000033
§ 371 (c)(1),
(2), (4) Date: Aug. 3, 2006

(87) PCT Pub. No.: WO2005/077191
PCT Pub. Date: Aug. 25, 2005

(65) Prior Publication Data
US 2008/0145480 A1    Jun. 19, 2008

Related U.S. Application Data

(60) Provisional application No. 60/544,908, filed on Feb. 12, 2004.

(30) Foreign Application Priority Data

Feb. 11, 2004 (DK) .................................. 2004 00206

(51) Int. Cl.
*A21D 8/04* (2006.01)

(52) U.S. Cl. .............................. 426/18; 426/64; 435/209

(58) Field of Classification Search .................... 426/18, 426/64; 435/209
See application file for complete search history.

(56) References Cited

FOREIGN PATENT DOCUMENTS

| CA | 2165839 | 6/1996 |
|---|---|---|
| WO | WO 95/01727 | 1/1995 |
| WO | WO 00/39289 | 7/2000 |
| WO | WO 03/106654 | 12/2003 |
| WO | WO 2004/023879 | 3/2004 |

OTHER PUBLICATIONS

Search results on SEQ. ID. No. 2, Xylanase of *Bacillus halodurans*, Accession No. AAM51802.*
JP2001245665, Oji Paper (2001) Abstract.
Nishimoto et al, Journal of Bioscience and Bioengineering vol. 93, No. 4, pp. 428-430 (2002).
Maat et al, Xylans and Xylanases, pp. 349-360 (1992).
John Taylor, Bakery, pp. 19-21 (1998).
Takami et al, Nucleic Acids Research, vol. 28, No. 21 pp. 4317-4331 (2000).
Kubata et al., Biosci. Biotech. Biochem., vol. 56, No. 9, pp. 1463-1464 (1992).

* cited by examiner

*Primary Examiner* — D. Lawrence Tarazano
*Assistant Examiner* — Hamid R Badr
(74) *Attorney, Agent, or Firm* — Kristin J. McNamara

(57) ABSTRACT

A xylanase from *Bacillus halodurans* can increase the shelf life of baked products. More specifically, the xylanase in combination with a maltogenic amylase further improves the softness of bread crumb without having detrimental effects on elasticity.

6 Claims, No Drawings

SEQUENCE LISTING

```
<160> NUMBER OF SEQ ID NOS: 4

<210> SEQ ID NO 1
<211> LENGTH: 781
<212> TYPE: DNA
<213> ORGANISM: Bacillus halodurans
<220> FEATURE:
<221> NAME/KEY: CDS
<222> LOCATION: (58)..(687)
<220> FEATURE:
<221> NAME/KEY: sig_peptide
<222> LOCATION: (58)..(141)
<220> FEATURE:
<221> NAME/KEY: mat_peptide
<222> LOCATION: (142)..(687)

<400> SEQUENCE: 1
aatcgacaac aaacgtgtaa ataagtagta cgataaaaat tttgaggagg acgaatc          57 atg ttt aag ttc gtt acg aaa gtt ttg acg gta gta att gca gct aca       105
Met Phe Lys Phe Val Thr Lys Val Leu Thr Val Val Ile Ala Ala Thr
        -25                  -20                  -15 att agt ttt tgt ttg agt gca gta ccg gca agt gct aat acc tat tgg       153
Ile Ser Phe Cys Leu Ser Ala Val Pro Ala Ser Ala Asn Thr Tyr Trp
    -10                   -5                   -1   1 caa tat tgg acc gat ggt ggt gga aca gta aat gct aca aat gga cct       201
Gln Tyr Trp Thr Asp Gly Gly Gly Thr Val Asn Ala Thr Asn Gly Pro
 5                  10                  15                  20 ggt gga aat tac agt gtg aca tgg aga gat aca ggg aac ttt gtt gtc       249
```

```
                                                                -continued

Gly Gly Asn Tyr Ser Val Thr Trp Arg Asp Thr Gly Asn Phe Val Val
             25                  30                  35 ggt aaa ggc tgg gaa atc ggt tca cca aat cga acg atc cat tac aat      297
Gly Lys Gly Trp Glu Ile Gly Ser Pro Asn Arg Thr Ile His Tyr Asn
             40                  45                  50 gct ggt gtc tgg gaa ccg tct gga aat gga tat ttg act ctc tat ggg      345
Ala Gly Val Trp Glu Pro Ser Gly Asn Gly Tyr Leu Thr Leu Tyr Gly
             55                  60                  65 tgg aca agg aat cag ctc ata gaa tat tat gtc gtt gat aat tgg gga      393
Trp Thr Arg Asn Gln Leu Ile Glu Tyr Tyr Val Val Asp Asn Trp Gly
     70                  75                  80 act tac aga cct act gga acc cat cga ggc acc gtt gtc agt gat ggg      441
Thr Tyr Arg Pro Thr Gly Thr His Arg Gly Thr Val Val Ser Asp Gly
85                  90                  95                 100 gga aca tat gac atc tat acg act atg cga tac aat gca cct tcc att      489
Gly Thr Tyr Asp Ile Tyr Thr Thr Met Arg Tyr Asn Ala Pro Ser Ile
                105                 110                 115 gat ggg aca caa acg ttc caa cag ttc tgg agt gtg agg caa tcg aag      537
Asp Gly Thr Gln Thr Phe Gln Gln Phe Trp Ser Val Arg Gln Ser Lys
             120                 125                 130 aga ccg act gga aat aac gtt agc att acg ttt agc aac cac gtg aat      585
Arg Pro Thr Gly Asn Asn Val Ser Ile Thr Phe Ser Asn His Val Asn
             135                 140                 145 gcg tgg aga aat gca gga atg aat ctg gga agt agt tgg tct tac cag      633
Ala Trp Arg Asn Ala Gly Met Asn Leu Gly Ser Ser Trp Ser Tyr Gln
     150                 155                 160 gta tta gca aca gaa ggc tat caa agt agc ggg aga tcg aat gta acg      681
Val Leu Ala Thr Glu Gly Tyr Gln Ser Ser Gly Arg Ser Asn Val Thr
165                 170                 175                 180 gtt tgg tagaacgaga aagacggaat taactttctg aatatttaaa aacaaatcta      737
Val Trp ttgttgtgac gaacttaaga tttactcatt aagaagaatg aagc                    781
```

<210> SEQ ID NO 2
<211> LENGTH: 210
<212> TYPE: PRT
<213> ORGANISM: Bacillus halodurans

<400> SEQUENCE: 2

```
Met Phe Lys Phe Val Thr Lys Val Leu Thr Val Val Ile Ala Ala Thr
             -25                 -20                 -15

Ile Ser Phe Cys Leu Ser Ala Val Pro Ala Ser Ala Asn Thr Tyr Trp
         -10                  -5                  -1  1

Gln Tyr Trp Thr Asp Gly Gly Thr Val Asn Ala Thr Asn Gly Pro
5                   10                  15                  20

Gly Gly Asn Tyr Ser Val Thr Trp Arg Asp Thr Gly Asn Phe Val Val
             25                  30                  35

Gly Lys Gly Trp Glu Ile Gly Ser Pro Asn Arg Thr Ile His Tyr Asn
             40                  45                  50

Ala Gly Val Trp Glu Pro Ser Gly Asn Gly Tyr Leu Thr Leu Tyr Gly
             55                  60                  65

Trp Thr Arg Asn Gln Leu Ile Glu Tyr Tyr Val Val Asp Asn Trp Gly
     70                  75                  80

Thr Tyr Arg Pro Thr Gly Thr His Arg Gly Thr Val Val Ser Asp Gly
85                  90                  95                 100

Gly Thr Tyr Asp Ile Tyr Thr Thr Met Arg Tyr Asn Ala Pro Ser Ile
                105                 110                 115

Asp Gly Thr Gln Thr Phe Gln Gln Phe Trp Ser Val Arg Gln Ser Lys
```

-continued

```
                    120                 125                 130
Arg Pro Thr Gly Asn Asn Val Ser Ile Thr Phe Ser Asn His Val Asn
        135                 140                 145

Ala Trp Arg Asn Ala Gly Met Asn Leu Gly Ser Ser Trp Ser Tyr Gln
        150                 155                 160

Val Leu Ala Thr Glu Gly Tyr Gln Ser Ser Gly Arg Ser Asn Val Thr
165                 170                 175                 180

Val Trp

<210> SEQ ID NO 3
<211> LENGTH: 47
<212> TYPE: DNA
<213> ORGANISM: Artificial
<220> FEATURE:
<223> OTHER INFORMATION: Primer 1
<220> FEATURE:
<221> NAME/KEY: source
<222> LOCATION: (19)..(47)
<223> OTHER INFORMATION: B. halodurans

<400> SEQUENCE: 3
cattctgcag ccgcggccaa tacctattgg caatattgga ccgatgg             47

<210> SEQ ID NO 4
<211> LENGTH: 51
<212> TYPE: DNA
<213> ORGANISM: Artificial
<220> FEATURE:
<223> OTHER INFORMATION: Primer 2
<220> FEATURE:
<221> NAME/KEY: source
<222> LOCATION: (21)..(51)
<223> OTHER INFORMATION: B. halodurans

<400> SEQUENCE: 4
gcgttgagac gcgcggccgc cattcttctt aatgagtaaa tcttaagttc g         51
```

PREPARATION OF DOUGH-BASED PRODUCT

CROSS-REFERENCE TO RELATED APPLICATIONS

This application is a 35 U.S.C. 371 national application of PCT/DK2005/000033 filed Jan. 20, 2005, which claims priority or the benefit under 35 U.S.C. 119 of Danish application No. PA 2004 00206 filed Feb. 11, 2004 and U.S. provisional application No. 60/544,908 filed Feb. 12, 2004, the contents of which are fully incorporated herein by reference.

FIELD OF THE INVENTION

The present invention relates to a process for preparing a dough-based product and to a dough composition.

BACKGROUND OF THE INVENTION

JP 2001-245665A (Oji Paper) describes a xylanase from *Bacillus halodurans* and its amino acid sequence. H. Takami et al., *Nucl. Acid Res.* 28 (21), 4317 (2000) describes the complete genome sequence of *B. halodurans*; it is included in the TrEMBL database with the accession number Q9KEF3. WO 0039289 describes the use of a xylanase from *Bacillus subtilis* for preparing dough.

SUMMARY OF THE INVENTION

The inventors have found that a xylanase from *Bacillus halodurans* can increase the shelf life of baked products. More specifically, the xylanase in combination with a maltogenic amylase further improves the softness of bread crumb without having detrimental effects on elasticity.

Accordingly, the invention provides a process for preparing a dough-based product, comprising adding a xylanase with a high identity to SEQ ID NO: 2 to a dough, leavening, and heating the dough. More specifically, the xylanase is a polypeptide which has at least 85% identity to the amino acid sequence as shown in positions 1-182 of SEQ ID NO: 2 or is encoded by a DNA sequence which can hybridize at 41° C. to the complementary strand of nucleotides 142-687 of SEQ ID NO: 1. The xylanase may be a polypeptide having an amino acid sequence which can be obtained from the mature polypeptide of SEQ ID NO: 2 by substitution, deletion, and/or insertion of one or more amino acids or be encoded by a polynucleotide having a sequence that can be derived from SEQ ID NO: 1 by substitution, deletion, and/or insertion of one or more nucleotides.

The invention further provides a dough composition which comprises flour together with the xylanase and a dough and/or bread-improving additive comprising the xylanase in the form of a granulate or agglomerated powder.

DETAILED DESCRIPTION OF THE INVENTION

Genomic DNA Source

A donor strain *B. halodurans* C-125 containing the xylanase gene Q9KEF3 is obtainable from Japan Collection of Microorganisms (JCM), RIKEN (The Institute of Physical and Chemical Research), 2-1 Hirosawa, Wako, Saitama 351-0198, Japan with accession number JCM 9153.

It is also available under accession number BAA-125 from American Type Culture Collection (ATCC) or LGC Promochem, Queens Road, Teddington, Middlesex TW11 0LY, UK.

Xylanase

The xylanase used in the invention is a polypeptide which has at least 85% identity to the amino acid sequence as shown in positions 1-182 of SEQ ID NO: 2 or is encoded by a DNA sequence which can hybridize at 41° C. to the complementary strand of nucleotides 142-687 of SEQ ID NO: 1. The xylanase can be produced as described in the examples or in JP 2001-245665A (Oji Paper).

Alignment and Identity

The polypeptide and polynucleotide of the invention may have identities to the disclosed sequences of at least 85%, particularly at least 90%, e.g. at least 95%.

For purposes of the present invention, the alignments and identities of the protein sequences are analysed by Vector NTI-program (Invitrogen Corporation). The alignments are created using the Clustal W algorithm (Nucleic Acid Research, 22 (22): 4673-4680, 1994). Alignment Parameters used for polypeptide alignments are: penalty for the first residue in a gap 10, penalty for additional residues in a gap 0.1, no penalty for gaps introduced at the end of a sequence Hybridization Suitable conditions for determining hybridization between a nucleotide probe and a homologous DNA or RNA sequence involve presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6-13), $^{32}$P-dCTP-labeled (specific activity>1×10$^9$ cpm/µg) probe for 12 hours at approx. 45° C. The filter is then washed two times for 30 minutes in 0.1×SSC, 0.5% SDS at a temperature of 30° C., 35° C., 41° C., 45° C. or 50° C. Molecules to which the oligonucleotide probe hybridizes under these conditions may be detected using a x-ray film.

Dough and/or Bread-Improving Additive

The xylanase may be provided as a dough and/or bread improving additive in the form of a granulate or agglomerated powder. The dough and/or bread improving additive may have a narrow particle size distribution with more than 95% (by weight) of the particles in the range from 25 to 500 µm.

Granulates and agglomerated powders may be prepared by conventional methods, e.g. by spraying the amylase onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy.

Flour Composition or Dough

The flour composition may particularly comprise wheat flour. It may a dry mixture comprising flour and the xylanase, particularly in the form of the additive described above. The flour composition may also be a dough, which may be fresh, frozen or par-baked. It may be a laminated dough.

The xylanase may be added to the flour composition or dough at a dosage of 0.1-10 mg enzyme protein per kg of flour, particularly 0.2-5 mg/kg.

The dough may also comprise other conventional dough ingredients, e.g. proteins, such as milk powder and gluten; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate. The dough may comprise fat (triglyceride) such as granulated fat or shortening.

Additional Enzyme

Optionally, one or more additional enzymes may be added to the dough together with the xylanase of the invention. The additional enzyme may be an amylase, a lipolytic enzyme (e.g. as described in WO 9953769) or a second xylanase.

The amylase may be an exo-acting maltogenic alpha-amylase. An example is a maltogenic alpha-amylase from *B. stearothermophilus* strain NCIB 11837, available from Novozymes A/S under the tradename Novamyl®; described in WO 9104669 and having the amino acid sequence shown as SEQ ID NO: 1 of U.S. Pat. No. 6,162,628A1. Another example is a Novamyl variant, e.g. as described in WO 9943794. The maltogenic amylase may be added at a dosage of 100-1000 MANU per kg flour (MANU activity unit defined in WO 9104669).

Dough-Based Product

The invention provides a method for preparing a dough-based product by leavening the dough and heating it, e.g. by baking or steaming. The dough may be leavened e.g. by adding chemical leavening agents or yeast, usually *Saccharomyces cerevisiae* (baker's yeast). The product may be of a soft or a crisp character, either of a white, light or dark type. Examples are steamed or baked bread (in particular white, whole-meal or rye bread), typically in the form of loaves or rolls.

EXAMPLES

Example 1

Production of Xylanase

Microbial Strain

*B. subtilis* PL1801. This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315-4321).

Competent *B. subtilis* cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296-304.

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990).

Enzymes for DNA manipulations were used according to the specifications of the suppliers (e.g. restriction endonucleases, ligases etc. are obtainable from New England Biolabs, Inc.).

Media

TY (as described in Ausubel, F. M. et al. (eds.) "Current protocols in Molecular Biology". John Wiley and Sons, 1995). LB agar (as described in Ausubel, F. M. et al. (eds.) "Current protocols in Molecular Biology". John Wiley and Sons, 1995). LBPG is LB agar supplemented with 0.5% Glucose and 0.05 M potassium phosphate, pH 7.0. BPX media is described in EP 0 506 780 (WO 91/09129).

Expression of Putative Xylanase Q9KEF3 from *Bacillus halodurans* in *Bacillus subtilis*

In order to express the xylanase gene in *B. subtilis* the gene was cloned into the plasmid expression vector pMOL944 (WO 00/75344 A1). It was cloned in such a way that the part of the gene encoding the mature enzyme was fused to the signal peptide from the amylase gene on the expression vector.

Propagation of the Donor Strain.

The strain *Bacillus halodurans* C-125 was propagated in liquid TY medium adjusted to approx. pH 9 by addition of 5% $Na_2CO_3$. After 18 hours of incubation at 37° C. and 300 rpm the cells were harvested and genomic DNA was isolated by the method below.

Genomic DNA Preparation

The *Bacillus halodurans* strain was propagated in liquid media as described above. The cells were harvested and genomic DNA was isolated by the method described by Pitcher et al. Chromosomal DNA from *Bacillus halodurans* was isolated (C-125). The xylanase gene was amplified by PCR using Primers 1 and 2 (SEQ ID NO: 3 and 4).

Restriction sites SacII and NotI are present at nucleotides 11-16 of SEQ ID NO: 3 and 13-20 of SEQ ID NO: 4. Nucleotides 19-47 of SEQ ID NO: 3 are identical to nucleotides 142-170 of SEQ ID NO: 1. Nucleotides 21-51 of SEQ ID NO: 4 are complementary to nucleotides 747-777 of SEQ ID NO: 1.

This creates a DNA fragment of approx. 700 bp. The fragment was cut by restriction enzymes SacII and NotI. Plasmid vector pMOL944 was isolated and cut by restriction enzymes SacII and NotI. The vector fragment (approx. 4.8 kb) and the PCR fragment was ligated and the ligation mixture was used to transform competent *B. subtilis* PL1801 cells. Selection for transformants was performed on LB agar plates containing Kanamycin (10 micro-g/ml). The resulting strain PL3522-3 showed increased xylan clearing zones as compared to the non-transformed host when plated on LB agar plates containing 0.2% AZCL-xylan (Megazyme) and Kanamycin (10 micro-g/ml). In order to produce the xylanase enzyme the strain PL3522-3 was inoculated in BPX medium at 30 C and 300 rpm for 4 days. The xylanase can be extracted from the supernatant of the culture medium.

Example 2

Effect of Xylanase on Freshness of Bread

Bread were baked according to the sponge & dough method.

| Recipes | |
|---|---|
| | % on flour basis |
| Sponge | |
| Soya oil | 2.5 |
| SSL | 0.38 |
| Yeast | 5 |
| Wheat flour | 60 |
| Water | 62 |
| Dough | |
| Ascorbic acid | optimized for each flour |
| ADA | 20 ppm |
| Salt | 2 |
| Syrup | 7 (dry substance) |
| Water | to be optimized for each flour |
| Wheat flour | 40 |
| Calcium propionate | 0.25 |

Sponge

Scaling of ingredients, addition of yeast, water, flour, SSL and oil into mixer bowl Mixing 90 rpm for 1 minutes, 150 rpm for 4 minutes. The sponge was weighted, the temperature was measured and the sponge was placed in a bowl~fermentation 3 hours at 27 C, 86% RH Dough Addition of ingredients and the sponge into the mixer bowl. The sponge and ingredients were mixed together 90 rpm for 9 minutes The temperature was measured, dough characteristics were evaluated, the dough was scaled into smaller pieces of 435 g each.

The dough rests on the table for 10 minutes

Doughs were sheeted and molded.

Fermentation for 55 minutes at 42 C and 86% RH.

Bread were baked at 200 C for 22 minutes

Enzymes were dosed at 1 mg of xylanase of the invention per kg of flour together with 400 MANU/kg of Novamyl. A control was made with 400 MANU/kg of Novamyl alone.

Bread were stored at room temperature until analysis.

Texture and water migration by NMR were measured on day 7, 14 and 21. A small sensory evaluation of softness and moistness was performed on day 21.

Results

Firmness of the loaves was measured as described in WO 9953769. The results were as follows:

| Novamyl dosage MANU/kg | Xylanase of invention mg/kg | Firmness after 7 days g | Firmness after 14 days g | Firmness after 21 days g |
|---|---|---|---|---|
| 400 | 1 | 427 | 560 | 758 |
| 400 | 0 | 481 | 576 | 836 |

Elasticity of the loaves was measured as described in U.S. Pat. No. 6,162,628. The results were as follows:

| Novamyl dosage MANU/kg | Xylanase of invention mg/kg | Elasticity after 7 days % | Elasticity after 14 days % | Elasticity after 21 days % |
|---|---|---|---|---|
| 400 | 1 | 52.7 | 49.2 | 46.2 |
| 400 | 0 | 52.7 | 50.1 | 46.0 |

The data show that the xylanase of the invention has a significant effect on firmness in combination with Novamyl. Elasticity is only slightly reduced The mobility of free water was determined as described by P. L. Chen, Z. Long, R. Ruan and T. P. Labuza, Nuclear Magnetic Resonance Studies of water Mobility in Bread during Storage. Lebensmittel Wissenschaft und Technologie 30, 178-183 (1997). The results were as follows:

| Novamyl dosage MANU/kg | Xylanase of invention mg/kg | Free water after 7 days microseconds | Free water after 14 days microseconds | Free water after 21 days microseconds |
|---|---|---|---|---|
| 400 | 1 | 8139 | 7354 | 6719 |
| 400 | 0 | 8067 | 7169 | 6541 |

The amount of free water has been described in literature to correlate to moistness of bread crumb. The data show that the xylanase is able to improve moistness measured by NMR when dosed on top of Novamyl.

The ranking from the small sensory evaluation of softness and moistness on day 21 showed that bread crumb made with the xylanase of the invention together with Novamyl was perceived as more moist than bread made with Novamyl alone.

The invention claimed is:

1. A process for preparing a dough-based product, comprising adding a xylanase and an exo-acting maltogenic alpha-amylase to a dough, leavening, and heating the dough, wherein the xylanase is a polypeptide having at least 90% identity to the amino acid sequence as shown in positions 1-182 of SEQ ID NO: 2.

2. A composition which comprises flour together with a xylanase which is a polypeptide having at least 90% identity to the amino acid sequence as shown in positions 1-182 of SEQ ID NO: 2, and an exo-acting maltogenic alpha-amylase.

3. The composition of claim 2, which is a dough.

4. A granulate or agglomerated powder comprising a xylanase which is a polypeptide having at least 90% identity to the amino acid sequence as shown in positions 1-182 of SEQ ID NO: 2, and an exo-acting maltogenic alpha-amylase.

5. The process of claim 1, wherein the xylanase is a polypeptide having at least 95% identity to the amino acid sequence as shown in positions 1-182 of SEQ ID NO: 2.

6. The composition of claim 2, wherein the xylanase is a polypeptide having at least 95% identity to the amino acid sequence as shown in positions 1-182 of SEQ ID NO: 2.

* * * * *